(12) United States Patent
Van Zon et al.

(10) Patent No.: US 9,612,239 B2
(45) Date of Patent: Apr. 4, 2017

(54) SUBSTANCE DETERMINING APPARATUS

(75) Inventors: Joannes Baptist Adrianus Dionisius Van Zon, Waalre (NL); Toon Hendrik Evers, Eindhoven (NL); Ron Martinus Laurentius Van Lieshout, Geldrop (NL); Wilhelmina Maria Hardeman, Eindhoven (NL); Derk Jan Wilfred Klunder, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 378 days.

(21) Appl. No.: 14/001,566

(22) PCT Filed: Feb. 27, 2012

(86) PCT No.: PCT/IB2012/050892
§ 371 (c)(1),
(2), (4) Date: Jan. 29, 2014

(87) PCT Pub. No.: WO2012/117332
PCT Pub. Date: Sep. 7, 2012

(65) Prior Publication Data
US 2014/0134602 A1    May 15, 2014

(30) Foreign Application Priority Data

Feb. 28, 2011 (EP) .................... 11156257
Apr. 21, 2011 (EP) .................... 11163337

(51) Int. Cl.
*G01N 21/17* (2006.01)
*G01N 33/543* (2006.01)
(Continued)

(52) U.S. Cl.
CPC ..... *G01N 33/54326* (2013.01); *G01N 21/552* (2013.01); *G01N 21/648* (2013.01); *G01N 21/7703* (2013.01); *G01N 27/745* (2013.01)

(58) Field of Classification Search
None
See application file for complete search history.

(56) References Cited

U.S. PATENT DOCUMENTS

| 2001/0002315 A1* | 5/2001 | Schultz | ................ B82Y 30/00 436/172 |
| 2003/0153023 A1 | 8/2003 | Starzl | |
| 2005/0112784 A1* | 5/2005 | Yguerabide | ......... C12Q 1/6816 436/518 |

FOREIGN PATENT DOCUMENTS

| WO | 2009093160 A1 | 7/2009 |
| WO | 2009098623 A1 | 8/2009 |

OTHER PUBLICATIONS

Van Ommering, Kim et al Mobility and Height Detection of Particle Labels in an Optical Evanescent Wave Biosensor with Single-Label Resolution Journal of Physics D Applied Physics, vol. 43, 2010, pp. 1-8.

\* cited by examiner

*Primary Examiner* — Rebecca Martinez (57) ABSTRACT

The invention relates to a substance determining apparatus (19) for determining a substance within a fluid. A location event determination unit (34) determines location events indicating that a particle, which may have attached the substance, is located in a sensing region and a property of the location events from the sensing signal generated by sensing the sensing region. A location events selection unit (70) selects a part of the location events having a property in a predefined property range, and a substance determination unit (40) determines the substance within the fluid (3) based on the selected part of the location events. This allows tuning the determination of the substance within the fluid to a desired property range, which can relate to a desired kind of bound particles, thereby reducing the influence of unwanted

(Continued)

effects on the determination of the substance and, thus, improving the determination accuracy.

11 Claims, 6 Drawing Sheets

(51) Int. Cl.
*G01N 21/552* (2014.01)
*G01N 21/64* (2006.01)
*G01N 21/77* (2006.01)
*G01N 27/74* (2006.01)

SUBSTANCE DETERMINING APPARATUS

CROSS-REFERENCE TO PRIOR APPLICATIONS

This application is the U.S. National Phase application under 35 U.S.C. §371 of International Application No. PCT/IB2012/050892 filed on Feb. 27, 2012, which claims the benefit of European Patent Application No. 11156257.5, filed on Feb. 28, 2011 and European Application No. 11163337.6, filed on Apr. 21, 2011. These applications are hereby incorporated by reference herein.

FIELD OF THE INVENTION

The invention relates to a substance determining apparatus and substance determining method for determining a substance within a fluid. The invention relates further to a binding device and an analyzing device for cooperating with each other for determining a substance within a fluid, an analyzing method for determining a substance within a fluid and an analyzing computer program for determining a substance within a fluid.

BACKGROUND OF THE INVENTION

WO 2009/098623 A1 discloses a magnetic biosensor based on magnetic beads that can be actuated with electromagnetic fields. The magnetic beads are functionalized with antibodies that can bind a specific analyte molecule in a sample. The beads are attracted to the sensor surface, where the number of bound beads is directly or inversely related to the amount of analyte molecules present in the sample. The beads are then detected by a technique which is based on frustrated total internal reflection (FTIR).

SUMMARY OF THE INVENTION

It is an object of the present invention to provide a substance determining apparatus and a substance determining method for determining a substance within a fluid, which allows increasing the accuracy of determining the substance. It is a further object of the present invention to provide a corresponding binding device and analyzing device for cooperating with each other for determining a substance within a fluid, an analyzing method for determining a substance within a fluid, and an analyzing computer program for determining a substance within a fluid.

In a first aspect of the present invention a substance determining apparatus for determining a substance within a fluid is presented, wherein the substance determining apparatus comprises:
- particles for being attached to the substance within the fluid,
- a binding surface for binding the particles, if the particles have been attached to the substance,
- a sensing unit for sensing the particles within a sensing region on the binding surface, wherein the sensing unit is adapted to generate a sensing signal depending on the particles in the sensing region,
- a location event determination unit for determining location events indicating that a particle is located in the sensing region and a property of the location events from the generated sensing signal,
- a location events selection unit for selecting a part of the location events having a property in a predefined property range, and
- a substance determination unit for determining the substance within the fluid based on the selected part of the location events.

In the prior art bound particles are sensed and a substance within the fluid, in particular, the amount or concentration of the substance within the fluid, is determined based on the bound particles. However, during a procedure of determining a substance within a fluid, particles may enter the sensing region and may leave the sensing region. Therefore, during this procedure, a number of location events can be determined being much larger than the number of particles bound at a certain measurement time. The determination of the substance within the fluid can therefore be based on a very large amount of data, if the determination is based on the location events. This large amount of data can improve the signal-to-noise ratio and, thus, increase the accuracy of determining the substance within the fluid. Moreover, since the location event selection unit selects a part of the location events having a property in a predefined property range, wherein the substance determination unit determines the substance within the fluid based on the selected part of the location events, the determination of the substance within the fluid can be tuned to a desired property range, which can relate to a desired kind of bound particles. The substance determination unit may then substantially only use the location events, which have certain properties, and substantially not other location events, which may be caused by other unwanted kinds of bound particles, scratches on the binding surface, dust on the binding surface, free particles, et cetera. This can lead to a further improvement of the accuracy of determining the substance within the fluid.

A location event corresponds to a location of the respective particle in the sensing region, wherein the respective particle can be located directly on or close to the binding surface. The location events can relate, for example, to binding events, i.e. to bound particles, or to free particles on or close to the binding surface.

The sensing unit can be any unit which uses a technique that allows generating a sensing signal being dependent on the particles in the sensing region, wherein the sensing region is defined by the sensing unit. For example, if an interaction of the particles with an evanescent field is used for sensing the particles, the sensing region is defined by the evanescent field. The sensing region defines preferentially a volume on and above the binding surface, wherein a particle is sensed, if it is located within the volume.

Preferentially, the location events determination unit is adapted to determine at least one of the following properties of the respective location event: lifetime, starting moment, ending moment, size and positional variation of the respective particle in the sensing region. The location event determination unit can be adapted to determine several properties of a respective location event, wherein the location events selection unit is adapted to select a part of the location events having properties within the respective property ranges. In particular, the location event selection unit can be adapted to select a part of the location events having all properties, which have been determined by the location event determination unit, within the respective property ranges. The starting moment and/or the ending moment is preferentially determined with respect to a predefined reference time. Moreover, the positional variation can be, for example, the standard deviation of measured coordinates of the respective particle over time, wherein the mean can give the central position and the standard deviation can define the positional variation. However, the positional variation can also be determined in another way. For example, it can be the maximum deviation from the mean position defining the central position.

The lifetime of a location event is preferentially the time of a particle within the sensing region. The lifetime can therefore also be regarded as being a residence time.

The substance determining apparatus is preferentially a magnetic biosensor, wherein the particles are magnetic beads, i.e. nanoparticles, which label the substance. The magnetic beads are preferentially functionalized with an attaching element that can be attached to the substance being, for example, a specific analyte molecule. The attaching element is, for example, an antibody, a protein, DNA, an aptamer et cetera. The substance determination apparatus is preferentially adapted to perform a sandwich immunoassay.

It is preferred that the sensing unit is adapted such that the generated sensing signal is indicative of starting moments and ending moments of location events, wherein the location event determination unit is adapted to determine the lifetimes of location events by determining the starting moments and the ending moments of the location events from the generated sensing signal. A starting moment is preferentially defined by the time at which a particle enters the sensing region and an ending moment is preferentially defined by the time at which the particle, which had entered the sensing region, leaves the sensing region. If a particle is present within the sensing region at the end of the measurement of the sensing signal, an ending moment can be defined as the time, at which the measurement of the sensing signal is stopped. In an embodiment, the sensing unit is adapted such that the generated sensing signal is indicative of starting moments and ending moments of single location events, wherein the location event determination unit is adapted to determine the lifetimes of the location events by determining starting moments and ending moments of single location events from the generated sensing signal. In particular, the sensing unit can be adapted to generate images of the binding surface at different times as the sensing signal, wherein an image shows at which positions in the sensing region particles are located at a time, wherein the location event determination unit is adapted to determine the starting moments and the ending moments by comparing temporally consecutive images. This allows determining location events and lifetimes of the location events with low computational efforts by simply comparing temporally consecutive images. The positions are preferentially in-plane positions of the particles present within the sensing region, i.e. positions of the particles within a plane defined by the binding surface or being parallel to the binding surface.

The starting and ending moments can be defined with respect to a series of consecutive images. For example, an i-th image can define a starting moment and a j-th image can define an ending moment, wherein j is larger than i and wherein a reference time can be defined by the first image of the series. The positional variation in the sensing region may be determined by tracking the respective particle in the temporally consecutive images.

The location event determining unit can be adapted to determine the size of a respective location in the respective image as the property of the respective location event.

The substance determination unit is preferentially adapted to determine the amount or the concentration of the particles within the fluid.

It is further preferred that the sensing unit is adapted to generate images of the binding surface at different times as the sensing signal, wherein an image shows at which positions on the binding surface particles are located at a time, wherein the substance determination unit is adapted to determine the substance within the fluid based on location events, which succeed each other in the same region having a predefined size on the binding surface with a temporal duration being smaller than a predefined temporal duration threshold and which have lifetimes being smaller than a lifetime threshold.

Thus, the substance determination unit can be adapted to determine the substance within the fluid based on these lifetimes and the lifetimes within the predefined lifetime range.

In general not only particles bound to the binding surface will be detected but also particles which are very close to the binding surface. Basically particles are visible when they are present in the sensing region on the binding surface, for example, in the evanescent field of an incoming light beam in the case of a sensing based on influencing the evanescent field like FTIR or scattering within the evanescent field. These particles do not have a molecular bond to the surface but move in close proximity of the surface. They may be called 'free' particles. Due to their movement in and out of the sensing region, they correspond to particles with a very short lifetime. In essence it is not the lifetime of a real molecular bond but it is a lifetime in the sensing region. Since the particles move, they show up at continuously different positions. By filtering these short lifetimes from the signal, the contribution of these free particles to the signal can be removed or at least decreased. This can improve the quality of determining the substance within the fluid.

If the sensing unit is adapted to sense the particles by using light, the location event determination unit can be adapted to determine the intensity of the scattered light, while the respective particle is in the sensing region, as the property of the respective location event. Also bound particles have the possibility to move over a short distance because of the finite bond length. This can cause continuous changes in the sensing signal. Small particles which have an intensity slightly above the background signal can appear and disappear due to the intensity fluctuations, showing a similar behaviour as the free particles. There is however one large difference: the bound particles will appear and disappear at approximately the same position, i.e. within a same region having a predefined size, while the free particles will appear and disappear at different positions, i.e. not within a same region having the predefined size. The size of the same region can be determined by, for example, calibration measurements such that bound particles appear and disappear within a same region and the free particles appear and disappear within and outside a same region having the predefined size.

Thus, if the substance determination unit is adapted to determine the substance within the fluid based on location events, which succeed each other in the same region on the binding surface with a temporal duration being smaller than a predefined temporal duration threshold and which have lifetimes being smaller than a lifetime threshold, bound fluctuating particles can be discriminated from free fluctuating particles. This measure can therefore further improve the quality of the sensing signal.

It is also preferred that the sensing unit comprises a light source for generating radiation for being directed to the binding surface for generating an evanescent field, which defines the sensing region, and a light detector for detecting light from the binding surface, wherein the detected light has been influenced by the particles located on the binding surface by influencing the evanescent field and wherein the images are generated from the detected influenced light. The light source preferentially comprises a light emitting diode or a laser for exciting the evanescent field. The sensing unit preferentially comprises an objective lens for collecting the light of the evanescent field scattered by particles in the sensing region, wherein the collected scattered light is imaged onto a two-dimensional light detector like a CCD- or CMOS-camera by an imaging unit like an imaging lens. This allows using dark field microscopy (DFM) for generating a sensing signal.

In a preferred embodiment, the sensing unit comprises a force applying unit for applying a force to the particles for putting bindings between the particles and the binding surface under stress, while sensing the particles.

The force applying unit is preferentially a magnetic unit for applying magnetic forces to the particles bound to the binding surface. The particles are preferentially particles which can be forced by a magnetic field. The magnetic unit can be adapted such that the particles can be attracted towards the binding surface or pulled away from the binding surface.

The substance determining apparatus is preferentially adapted to provide a binding phase and a washing phase. In the binding phase the force applying unit forces the particles towards the binding surface, in order to allow the particles to be bound to the binding surface, and preferentially the unbound particles away from the binding surface in an alternating way, i.e. in the binding phase preferentially the force applying unit forces the particles alternately towards the binding surface and away from the binding surface. In the binding phase particles can be bound to the binding surface and bindings can be broken. In the following washing phase the force applying unit applies a force to the particles, which urge the particles only away from the binding surface, thereby washing unbound particles away from the binding surface and putting the bindings between bound particles and the binding surface under stress. In the washing phase preferentially new bindings are not generated and also bound particles are released from the binding surface. The sensing unit can be adapted to sense the particles on the binding surface during the binding phase and/or during the washing phase, wherein the location event determination unit can be adapted to determine lifetimes of location events, in particular, of binding events, from the generated sensing signal in the binding phase and/or in the washing phase.

It is further preferred that the location event determination unit is adapted to
  determine a particles signal being indicative of the number of particles in the sensing region from the sensing signal,
  differentiate the particles signal, and
  determine a distribution of location events depending on their lifetimes in the sensing region from the differentiated particles signal,
wherein the location selection unit is adapted to select the part of the location events having a lifetime within a predefined lifetime range being the predefined property range based on the determined distribution of location events.

The particles signal can directly be the sensing signal or a processed sensing signal. Moreover, the distribution of location events depending on their lifetimes can be directly the differentiated particles signal or a processed differentiated particles signal.

The particles signal corresponds preferentially to a washing phase and can be indicative of the total number of particles in the sensing region, without comprising individual particle information, wherein the particles signal and the sensing signal are, for example, an FTIR signal. This allows providing a histogram of lifetimes of the location events in a technically relatively simple way. In particular, in this embodiment, it is not necessary to use a sensing unit, which is able to identify single location events. The substance within the fluid can also be determined based on a selected part of the location events, if the location event determination unit determines location events indicating that a particle is located in the sensing region on the binding surface and their lifetimes in the sensing region by determining the distribution of location events depending on their lifetimes, without determining single location events and the lifetimes of the single location events.

The predefined property range is preferentially predefined such that a figure of merit, which is indicative of a ratio of a specific histogram of a property of specific location events being binding events, which relate to bindings of particles having been attached to the substance, and a non-specific histogram of the property of non-specific location events, which relate to other location events, has an optimum within the predefined property range. The figure of merit is, for example, directly the mentioned ratio. Location events, which relate to other location events, are, for example, location events which relate to non-specific bindings of the particles, free particles, surface artifacts like scratches, et cetera. In an embodiment, a specific histogram of a property is determined based on a sensing signal, which has been generated while the substance was present within the fluid, and a non-specific histogram of a property is determined based on a sensing signal which has been generated while the substance was not within the fluid. The predefined property range can be predefined such that the ratio of these two histograms has a maximum within the predefined property range. For determining the specific histogram of a property the fluid comprises the substance in a concentration with a range of, for example, 1 fM to 10 pM. However the concentration can also be lower or larger. The predefined property range can be predefined such that a probability that a property of location events, which are related to at least one of unbound particles, other elements and artifacts on the binding surface, is not within the predefined property range is larger than a probability that a property of location events, which are related to at least one of unbound particles, other elements and artifacts on the binding surface, is within the predefined property range. In particular, the predefined property range is preferentially predefined such that a property of location events, which are related to at least one of unbound particles, other elements and artifacts on the binding surface, are substantially not within the predefined property range.

The substance determination apparatus preferentially comprises a binding device, in particular, a cartridge, including the particles and the binding surface and being adapted to receive the fluid, and an analyzing device, which can be regarded as a reader, including the sensing unit, the location event determination unit, the location events selection unit and the substance determination unit.

The binding device is preferentially a disposable device and the analyzing device is preferentially a reusable device. Thus, by distributing the functionalities over the binding device and the analyzing device, a part of the substance determination apparatus can be used as a disposable device and the other part can be used as a reusable device. Since the fluid, which is preferentially a sample of a bodily fluid like blood, saliva or urine, is introduced into the binding device and since the binding device is a disposable device, the binding device can be used only one time before being disposed, i.e. a determination of the substance within the fluid is not affected by impurities of a previous measurement.

In a further aspect of the present invention a binding device for cooperating with an analyzing device for determining a substance within a fluid is presented, wherein the binding device comprises
  particles for being attached to the substance within the fluid,
  a binding surface for binding the particles, if the particles have been attached to the substance,
  the analyzing device comprises:
  a sensing unit for sensing the particles within a sensing region on the binding surface, wherein the sensing unit is adapted to generate a sensing signal depending on the particles in the sensing region,
  a location event determination unit for determining location events indicating that a particle is located in the sensing region and a property of the location events from the generated sensing signal,
  a location events selection unit for selecting a part of the location events having a property in a predefined property range,
  a substance determination unit for determining the substance within the fluid based on the selected part of the location events.

In a further aspect of the present invention an analyzing device for cooperating with a binding device for determining a substance within a fluid is presented, wherein the binding device comprises:
  particles for being attached to the substance within the fluid,
  a binding surface for binding the particles, if the particles have been attached to the substance,
  the analyzing device comprises:
  a sensing unit for sensing the particles within a sensing region on the binding surface, wherein the sensing unit is adapted to generate a sensing signal depending on the particles in the sensing region,
  a location event determination unit for determining location events indicating that a particle is located in the sensing region and a property of the location events from the generated sensing signal,
  a location events selection unit for selecting a part of the location events having a property in a predefined property range,
  a substance determination unit for determining the substance within the fluid based on the selected part of the location events.

In a next aspect of the present invention a substance determining method for determining a substance within a fluid is presented, wherein the substance determining method comprises following steps:
  attaching particles to the substance within the fluid,
  binding the particles to a binding surface, if the particles have been attached to the substance,
  sensing the particles within a sensing region on the binding surface by a sensing unit, wherein a sensing signal is generated depending on the particles in the sensing region,
  determining location events indicating that a particle is located in the sensing region and a property of the location events from the generated sensing signal by a location event determination unit,
  selecting a part of the location events having a property in a predefined property range by a location events selection unit,
  determining the substance within the fluid based on the selected part of the location events by a substance determination unit.

In a further aspect of the present invention an analyzing method for cooperating with a binding method for determining a substance within a fluid is presented, wherein the binding method comprises following steps:
  attaching particles to the substance within the fluid,
  binding the particles to a binding surface, if the particles have been attached to the substance,
  the analyzing method comprising following steps:
  sensing the particles within a sensing region on the binding surface by a sensing unit, wherein a sensing signal is generated depending on the particles in the sensing region,
  determining location events indicating that a particle is located in the sensing region and a property of the location events from the generated sensing signal by a location event determination unit,
  selecting a part of the location events having a property in a predefined property range by a location events selection unit,
  determining the substance within the fluid based on the selected part of the location events by a substance determination unit.

In a further aspect of the present invention an analyzing computer program for determining a substance within a fluid is presented, wherein the computer program comprises program code means for causing an analyzing device described above to carry out the steps of the analyzing method described above, when the computer program is run on a computer controlling the analyzing device.

It shall be understood that the embodiments, including substance determining apparatus, the binding device, the analyzing device, the substance determining method, the analyzing method, and the analyzing computer program as described above, have similar and/or identical preferred embodiments, in particular, as defined in the dependent claims and described in the specification.

It shall be understood that a preferred embodiment of the invention can also be any combination of the dependent claims with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
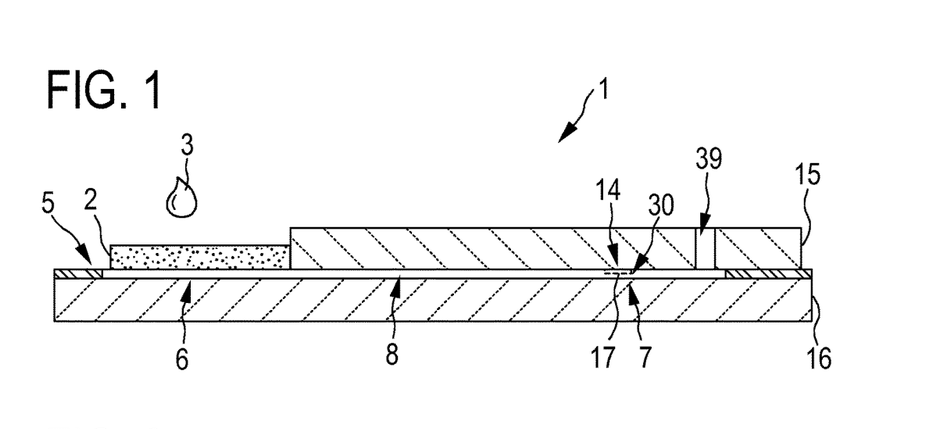
FIG. 1 shows schematically and exemplarily a cross-section of a binding device.

FIG. 1 shows schematically and exemplarily a binding device 1 for binding a substance, which has to be determined within a fluid 3. The binding device 1 comprises a filter element 2 for filtering the fluid 3 and a capillary structure 5 for generating capillary forces. The capillary structure 5 is attached to the filter element 2 by using preferentially an adhesive. The capillary structure 5 is, in this embodiment, made of a double-sided tape which is adhesive on two sides.

The binding device 1 comprises a filtering location 6 at which the filter 2 is located and a sensing location 7 at which a substance within the fluid 3 is detectable, wherein the capillary structure 5 is formed such that the filtered fluid 3 is guided from the filtering location 6 to the sensing location 7 by capillary forces.

Figure 2:
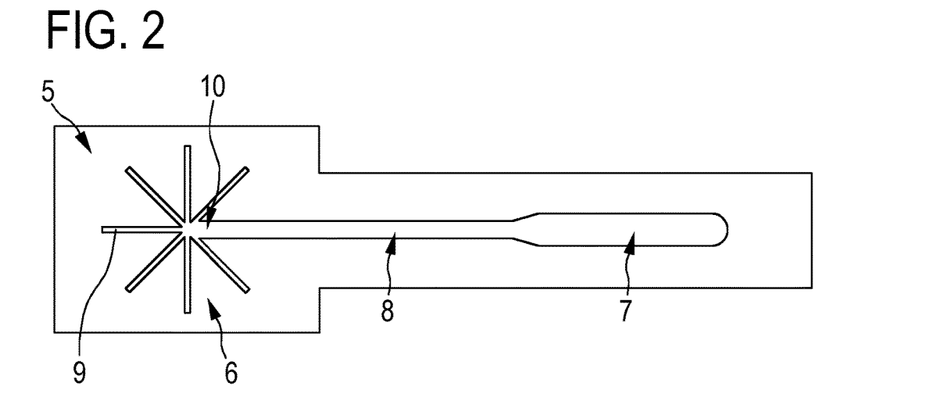
FIG. 2 shows schematically and exemplarily a capillary structure of the binding device.
Figure 3:
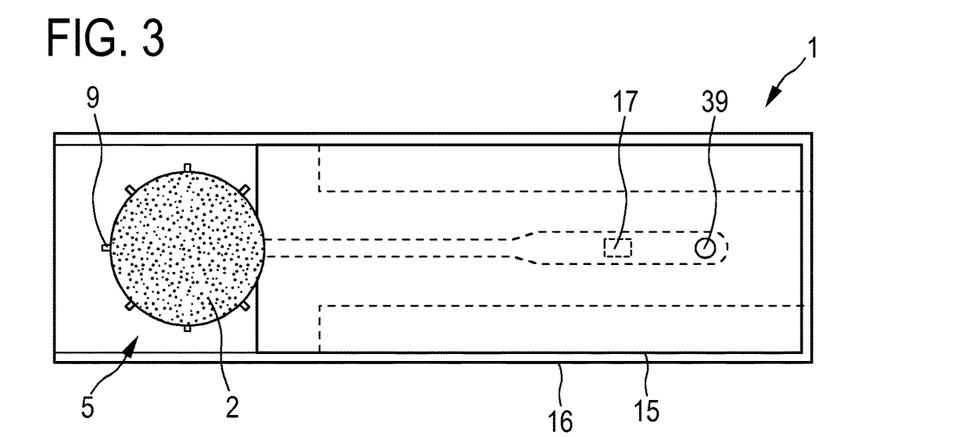
FIG. 3 shows schematically and exemplarily a top view on the binding device.

The capillary structure 5 comprises a collecting channel 8, which connects the filtering location 6 with the sensing location 7, and guiding channels 9 located at the filtering location 6, wherein the guiding channels 9 extend from an end of the connecting channel 8. In this embodiment the guiding channels 9 extend radially from the end 10 of the connecting channel 8. The capillary structure 5 is schematically and exemplarily shown in more detail in FIG. 2. FIG. 3 shows schematically and exemplarily a top view on the binding device 1 which is shown in a sectional view in FIG. 1.

The binding device 1 comprises a sensing cavity 14 which is located at the sensing location 7 and in which a substance of the fluid 3 is detectable. This sensing cavity 14 is formed by a first part 15 and a second part 16 of the binding device 1 together with the capillary structure 5. In addition, the first part 15 and the second part 16 form together with the capillary structure 5 the connecting channel 8. The first part 15 and the second part 16 are preferentially attached to each other via an adhesive, in particular, via the double-sided tape forming the capillary structure 5. The first part 15 and the second part 16 are plastics substrates which are injection molded and preferentially transparent to visible light. The first part 15 can be regarded as an upper substrate, closing element or cover element and the second part 16 can be regarded as a lower substrate or base element of the binding device 1. The first part 15 comprises a vent 39 for allowing a gas to leave the capillary structure 5.

In this embodiment, the filter element 2 is a blood separation filter and the binding device 1 forms a cartridge which is preferentially disposable. The binding device 1 is preferentially used in point-of-care diagnostics. The binding device 1 is preferentially adapted for detecting a low concentration biomarker in a sample of whole blood, in particular, in a finger prick sample of, for example, 25 µl. The sensing location 7 preferentially comprises an immunoassay. In particular, the sensing location 7 comprises a group 17 of particles for being attached to a substance within the fluid 3, wherein the group of particles mixes with the fluid 3, and the particles attach the substance within the fluid 3, if the fluid 3 is at the sensing location 7. The group 17 of particles can also be located between the sensing location 7 and the filtering location 6.

Figure 4:
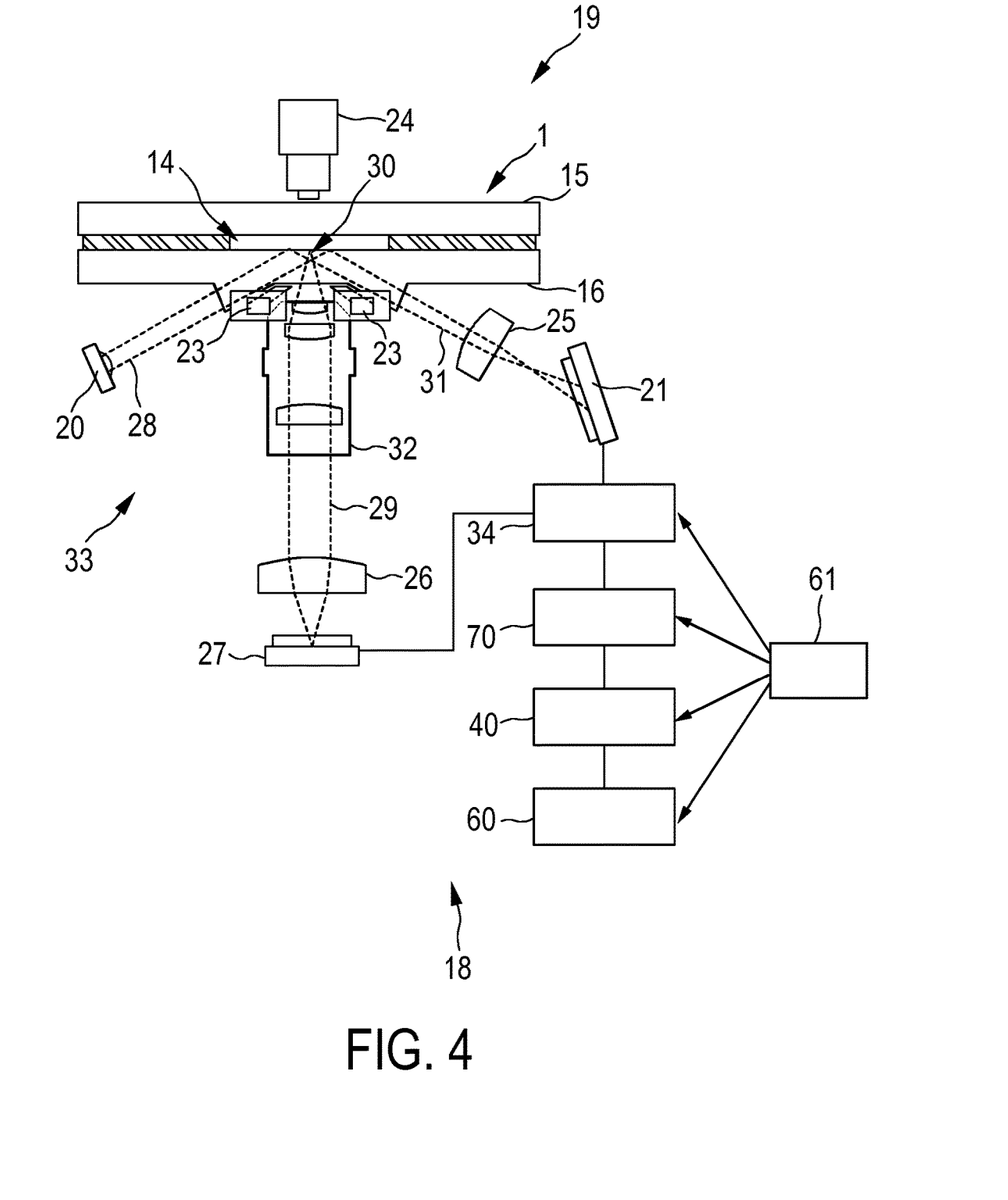
FIG. 4 shows schematically and exemplarily a substance determining apparatus comprising the binding device and an analyzing device.

FIG. 4 shows schematically and exemplarily a substance determining apparatus 19 comprising the binding device 1 and an analyzing device 18. The binding device 1 has been inserted into the analyzing device 18. The analyzing device 18 comprises a sensing unit 33 for sensing the particles 17 within a sensing region on the binding surface 30, wherein the sensing unit 33 is adapted to generate a sensing signal depending on the particles in the sensing region. The analyzing device 18 further comprises a location event determination 34 for determining location events indicating that a particle is located in the sensing region and their lifetimes in the sensing region from the generated sensing signal. Moreover, the analyzing device 18 comprises a location event selection unit 70 for selecting a part of the location events having a lifetime in a predefined lifetime range, and a substance determination unit 40 for determining the substance within the fluid 3 based on the selected part of the location events. Preferentially, the substance determination unit 40 is adapted to determine the amount and/or concentration of the substance within the fluid based on the determined location events.

The substance determining apparatus 19 is a magnetic biosensor, wherein the particles are magnetic beads, i.e. nanoparticles, which label the substance by being attached to the substance. For attaching the substance the magnetic beads are functionalized with an attaching element that can be attached to the substance being, for example, a specific analyte molecule. In this embodiment, the attaching element is an antibody. However, the attaching element can also be a protein, DNA, aptamer et cetera.

The sensing unit 33 comprises a magnetic unit 23, 24 for attracting the magnetic particles to the binding surface 30 and for pulling the magnetic particles away from the binding surface 30. The magnetic unit comprises a horseshoe magnet 23 being preferentially in a planar arrangement at one side of the binding device 1, if the binding device is inserted into the analyzing device, and a second magnet 24 being arranged on the opposite side of the binding device 1, if the binding device is inserted into the analyzing device. The magnetic unit 23, 24 is a force applying unit for applying a force to the particles bound to the binding surface 30.

The sensing unit 33 is preferentially adapted such that the generated sensing signal is indicative of starting moments and ending moments of single binding events. In particular, the sensing unit 33 is adapted to generate images of the binding surface 30 at different times as the sensing signal, wherein an image shows at which positions on the binding surface 30 particles are bound at a time.

In this embodiment, the sensing unit 33 comprises a light source 20 being, for example, a light emitting diode or a laser for generating radiation 28 for being directed to the binding surface 30 for generating an evanescent field on the binding surface 30. The evanescent field, which defines the sensing region, on the binding surface 30 is influenced by the particles located in the sensing region, thereby influencing a reflected light beam 31 comprising the light being total internally reflected at the cartridge surface, and a scattered light beam 29 comprising the light of the evanescent field scattered by the particles in the sensing region on the binding surface 30. The reflected light 31 is imaged by an objective lens 25 onto a first light detector 21 being preferentially a CCD camera. The scattered radiation is collected by a microscope objective lens 32 and imaged on a second detector 27 by an imaging lens 26. Also the second detector 27 is preferentially a CCD camera. The first detector 21 and the second detector 27 generate sensing signals which are provided to the location event determination unit 34 for determining location events indicating that a particle is located in the sensing region and for determining lifetimes of the location events from the generated sensing signal. The sensing signal of the first detector 21 is based on FTIR and the sensing signal generated by the second detector 27 is based on DFM.

At least one of the sensing signals of the first detector 21 and the second detector 27 forms images of the binding surface at different times showing at which positions on the binding surface or in a plane parallel to the binding surface the particles are located in the sensing region at the different times. The sensing unit can comprise elements for detecting the sensing signal of the first detector or the second detector only, i.e. the detection system for detecting the FTIR sensing signal or the detection system for detecting the DFM sensing signal can be omitted. In a preferred embodiment, the sensing unit only comprises the detection system for generating the DFM sensing signal based on the light of the evanescent field scattered by the particles located in the sensing region.

In the following the generation of the sensing signals will be described in more detail. If a beam of light reflects on the interface between a medium with a higher refractive index, for example the second part 16, and a lower refractive index, for example the fluid, there is a certain critical angle of incidence above which there is a situation of total internal reflection (TIR). The detection configuration (regarding refractive indices and angle of incidence) shown in FIG. 4 is such that there is total internal reflection of the incoming beam. Although the light is totally reflected in such a situation, there is still penetration of the light in a very thin layer of the medium with the low refractive index. This is called an evanescent field, the intensity of which decays exponentially in the low refractive index medium with a characteristic penetration depth of the order of the wavelength of the light. In practice the penetration depth is preferentially less than 0.5 micrometer. If magnetic particles are within the evanescent field, i.e. within the sensing region, for example, if magnetic particles are bound to the binding surface 30, the optical properties of this very thin first fluid layer of preferentially about 0.5 micrometer are changed leading to a reduction of the intensity of the reflected light beam. This is caused by absorption and scattering of the evanescent light (FTIR; frustrated total internal reflection). As a result the light intensity, and hence the signal, at the detector 21 decreases, whereas the light intensity, and hence the signal, at the detector 27 increases.

The location event determination unit 34 is preferentially adapted to determine the lifetimes of location events by determining the starting moments and the ending moments of single location events at the different positions in the sensing region from the generated sensing signal. In particular, the location event determination unit 34 is adapted to determine the starting moments and the ending moments by comparing temporally consecutive images of the binding surface generated at different times by the first detector 21 or the second detector 27. The lifetime generally depends on the kind of binding, for example, specific or non-specific binding. The lifetime can also depend on whether the respective location event has been generated by a free particle or a bound particle which may fluctuate because of a finite binding length. A location event can also be generated by artifacts on the binding surface like scratches or dust, wherein then the lifetime of the location event is expected to be relatively long.

Figure 5:
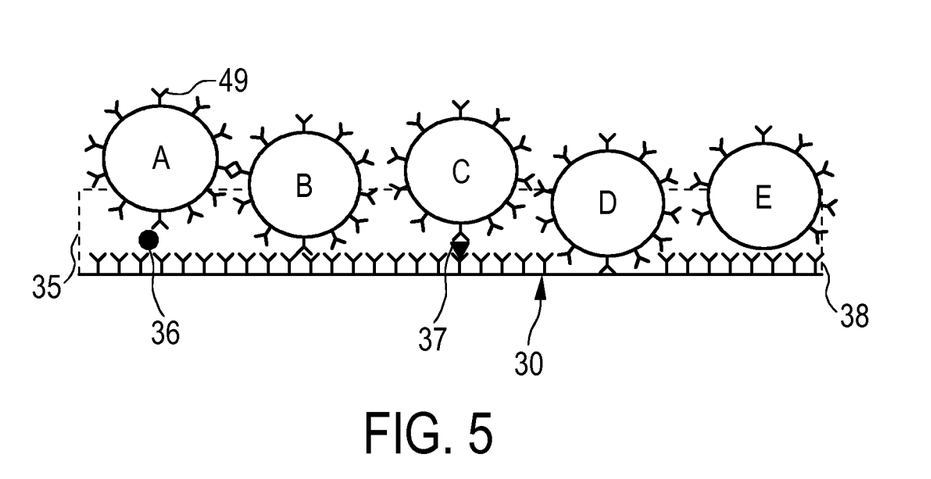
FIG. 5 shows schematically and exemplarily different kinds of binding to a binding surface.

FIG. 5 shows schematically and exemplarily different kinds of binding on the binding surface 30. In FIG. 5 the broken line 35 indicates schematically and exemplarily a height of the evanescent field, i.e. a sensing region, which can be defined as a decay length $\zeta$ of the evanescent field.

The particle indicated by A is specifically bound to the binding surface 30 via the attaching element 49, the substance 36 and the binding element 38. The particle B does not form a normal sandwich like the particle A, but is bound to the binding surface 30 via the attaching element 49 and the binding element 38, i.e. without a sandwiched substance.

The particle C is bound to the binding surface 30 via the attaching element 49, an element 37 not being the substance to be determined, i.e. not being the analyte, and the binding element 38. The particle D is directly bound to an exposed area on the binding surface 30 via the attaching element 49. This means, the binding surface 30 comprises the binding elements 38 for forming a normal sandwich as shown in FIG. 5 for the particle A. These binding elements 38 also bind particles B, C and E in the example shown in FIG. 5. However, the particle D is directly bound to the binding surface 30 via the attaching element 49.

An exposed area of the particle E is bound to the binding surface 30 directly via the binding elements 38, i.e. the particles comprise attaching elements 49 for attaching the substance, wherein the particles A, B, C, D are bound to the binding surface 30 via the attaching elements 49 of the respective particle. However, the particle E is not bound to the binding surface 30 via the attaching elements 49, but an exposed area of the particle E is attached to the binding surface 30 via the binding element 38.

In FIG. 5, only the particle A forms a normal sandwich. The particle A is therefore specifically bound to the binding surface 30. The other particles B, C, D, E do not form a normal sandwich and are therefore non-specifically bound to the binding surface 30.

These different kinds of binding are generally related to different lifetimes. Thus, by selecting only location events with lifetimes within a predefined lifetime range which corresponds to a desired kind of binding, in particular, to a specific binding, an amount or a concentration of the substance within the fluid can be determined based on this specific binding, wherein the accuracy of the determination of the amount or concentration can be less effected by other kinds of binding like non-specific bindings.

A non-specific location event is preferentially any location event that is not dependent on the presence of the substance, i.e. on the presence of the specific analyte that is to be detected in the sample fluid. In particular, a non-specific binding is preferentially any binding that is not dependent on the presence of the substance. FIG. 5 illustrates differences between specific and non-specific bindings for a sandwich immunoassay. However, also other kinds of assay can comprise specific and non-specific binding and the substance determining apparatus can also be used to determine specifically bound particles if another assay is chosen for determining the substance in the fluid.

The sensing unit 33 is adapted such that sensing signals, i.e. signal changes, caused by single particles can be distinguished using the scattered light 29 collected by the microscope objective 32 and imaged onto the second light detector 27 by the imaging lens 26. The second light detector 27 comprises a two-dimensional detection surface 30 for generating images of the binding surface at different times. If at a certain position in the image a particle is detected and if at this position a particle was not detected in a temporally preceding image, a starting moment of a location event is detected, and, if at this position in a later image the particle has disappeared, the ending moment of this location event can be determined. Differences between the ending moments and the starting moments define the lifetime of the respective location events. Since these location events and the corresponding lifetimes are determined over some time and among the binding surface, a large amount of location events and corresponding lifetimes can be determined by the location event determination unit 34.

The substance determining apparatus 19 is preferentially adapted to provide a binding phase and a washing phase. In the binding phase the force applying unit forces the particles towards the binding surface, in order to allow the particles to be bound to the binding surface, and away from the binding surface to remove unbound particles in an alternating way. In the following washing phase the force applying unit applies a force to the particles, which urges the particles only away from the binding surface, thereby washing unbound particles away from the binding surface and putting the bindings between bound particles and the binding surface under stress. The stress can lead to a release even of bound particles. A distribution of location events and their lifetimes, in particular, a corresponding lifetimes histogram, can be determined in the binding phase or in the washing phase. If the histogram shall be determined in the binding phase, images of the binding surface are provided by the second detector at least at the times at which the unbound particles have been pulled away from the binding surface in the binding phase. Preferentially, consecutive images generated while the unbound particles are pulled away from the binding surface in the binding phase are compared for determining the lifetime of the location events. If a particle is visible at a certain position in a first image and at the same position not in a preceding image, the time of a starting moment can be detected. If at a certain position within a second image a particle is visible and if at the same certain position in a subsequent image a particle is not visible, the time of an ending moment can be determined. The determined starting and ending times can be used for determining lifetimes of single location events, wherein a histogram of these lifetimes can be formed. Thus, by using this single location event detection a lifetime distribution can be obtained during the binding phase and/or the washing phase.

A lifetime distribution can also be obtained based on ensemble information by using the FTIR signal detected by the detector 21. This will in the following exemplarily be described in more detail.

Once a particle has been bound to the binding surface, it will not remain in the bound state forever. Due to the presence of forces and thermal vibrations, the molecular bonds are constantly under stress, resulting in the continuous breakage of bonds. This breakage of bonds is a statistical process which can be described by a Poisson distribution. Assuming that a certain molecular bond has an average lifetime $<\tau>$, the fraction of particles which is still bound to the surface after a certain time t is given by:

$$f = e^{-t/<\tau>} \quad (1)$$

which is recognized as a Poisson distribution with average $\lambda = <\tau>$.

If it is assumed that N(0) is the number of particles bound to the surface at t=0 and that no new particles will bind to the surface for t>0, the number of particles present on the surface after a time t is given by:

$$N(t) = N(0) \cdot e^{-t/<\tau>} \quad (2)$$

Using this equation the lifetime distribution of the molecular bond can be calculated. The number of particles, $\Delta N$, which leaves the surface between t and t+$\Delta t$ (and thus has a lifetime t), is equal to $\Delta N = N(t) - N(t+\Delta t)$. The lifetime distribution, $\Delta N(t)$, can then be described by:

$$\Delta N(t) = N(t) - N(t + \Delta t) = -\frac{dN}{dt} \cdot \Delta t = \frac{N_0}{<\tau>} \cdot e^{-t/<\tau>} \cdot \Delta t. \quad (3)$$

This calculation shows that the lifetime distribution (also referred to as the residence time distribution) of a single molecular bond can be directly related to the Poisson distribution and has an exponentially decaying shape.

For determining a distribution of lifetimes of location events, a washing curve can be measured during the washing phase, in which a force directed away from the binding surface is applied to the particles in order to remove the unbound particles from the binding surface such that they cannot bind to the binding surface anymore. Furthermore the force stresses the bonds of the bound particles a little bit to stimulate their release. During the presence of this force the number of particles which are still bound to the surface, N(t), will decrease as a function of time (the so-called "washing curve"). This will yield the Poisson distribution mentioned in equation (2). Differentiation of the measured curve N(t) will yield the lifetime distribution. Because no particles bind to the surface during this washing phase, the density of the particle ensemble on the surface can be monitored to establish the washing curve. Density monitoring can be done using the above mentioned FTIR detection, another method for obtaining only ensemble information, or by a method which provides single particle information like the above mentioned DFM technique.

The location event determination unit 34 can therefore be adapted to determine a particles signal being indicative of the number of particles in the sensing region from the sensing signal, differentiate the particles signal, and determine a distribution of location events depending on their lifetimes in the sensing region from the differentiated particles signal, wherein the particles signal can directly be the sensing signal, for example, the FTIR signal. The location selection unit 70 is then adapted to select the part of the location events having a lifetime within the predefined lifetime range based on the determined distribution of location events.

Given the lifetime distribution, the original amount of particles having a molecular bond can be derived by integrating the lifetime distribution since $$\sum_{t=0}^{t=\infty} \Delta N(t) = N_0. \quad (4)$$

In case multiple molecular bond types are present such as specific and non-specific bonds, the measured lifetime distribution is a superposition of the lifetime distributions of the individual bonds, which will be exemplarily described in more detail in the following.

If it is assumed that there are two types of non-specific binding, one ($N_L$ particles) with a low residence time ($\tau_L$) and one ($N_H$ particles) with a high residence time ($\tau_H$), and that there is one type of specific binding ($N_M$ particles) which has a medium residence time, $\tau_M$, with $\tau_L < \tau_M < \tau_H$, the number of particles present on the surface is a superposition of equation (2) and can be given by:

$$N(t) = N_L \cdot e^{-t/\tau_L} + N_M \cdot e^{-t/\tau_M} + N_H \cdot e^{-t/\tau_H} \quad (5)$$

According to equation (3) the lifetime distribution of the ensemble will have the form:

$$\Delta N(t) = \frac{N_L}{\tau_L} \cdot e^{-t/\tau_L} + \frac{N_M}{\tau_M} \cdot e^{-t/\tau_M} + \frac{N_H}{\tau_H} \cdot e^{-t/\tau_H}. \qquad (6)$$

Integration over all available lifetimes $(0, \infty)$ would yield the total amount of particles equal to $N_L + N_M + N_H$. Instead of integrating over all available lifetimes, a limited lifetime interval $(t_1, t_2)$ is chosen. The purpose of this limited interval is to better select the specific bonds having an average lifetime $\tau_M$ which lies between $\tau_L$ and $\tau_H$.

Integrating equation (6) over the limited lifetime interval $(t_1, t_2)$ yields $$\Delta N = N_L \cdot (e^{-t1/\tau_L} - e^{-t2/\tau_L}) + N_M \cdot (e^{-t1/\tau_M} - e^{-t2/\tau_M}) + N_H \cdot (e^{-t1/\tau_H} - e^{-t2/\tau_H}) \qquad (7)$$

where the three different terms represent the number of particles having a particular bond.

Preferentially, the filtering, i.e. the selection of a part of the location events having a lifetime in a predefined lifetime range, is performed such that the contribution of the non-specific bonds (the terms containing $N_L$ and $N_H$) is small with respect to the term with the specific bonds. If the terms containing $N_L$ and $N_H$ are small, in particular, vanish, in equation (7), the value $\Delta N$ is less influenced by non-specific bonds and comprises therefore an improved quality. This, in turn, improves the quality of a determined concentration or amount of specifically bound particles determined based on the filtered location events.

As a figure of merit (FOM) for the effect of the filtering, the ratio of specific binding to non-specific binding can be defined. According to equation (7) this ratio is equal to:

$$FOM = \frac{N_M \cdot (e^{-t1/\tau_M} - e^{-t2/\tau_M})}{N_L \cdot (e^{-t1/\tau_L} - e^{-t2/\tau_L}) + N_H \cdot (e^{-t1/\tau_H} - e^{-t2/\tau_H})}. \qquad (8)$$

The predefined lifetime range $(t_1, t_2)$ is preferentially predefined such that a figure of merit, which is indicative of a ratio of a specific histogram of lifetimes of specific location events being binding events, which relate to bindings of particles having been attached to the substance, and a non-specific histogram of lifetimes of non-specific location events, which relate to other location events, has an optimum within the predefined lifetime range.

For example, the figure of merit can be measured by performing two measurements, a first measurement with the substance within the fluid and a second measurement without the substance within the fluid. The second measurement can be regarded as being a blank measurement. For each of these measurements, a histogram of lifetimes of location events is determined for generating a first lifetime histogram resulting from the first measurement and a second lifetime histogram resulting from the second measurement. A ratio of the first lifetime histogram and the second lifetime histogram is calculated and this ratio can be regarded as being a figure of merit, wherein it is assumed that the result of the second measurement is mainly caused by non-specific location events. The predefined lifetime range is then preferentially predefined such that a maximum of this ratio is within this lifetime range.

Figure 6:
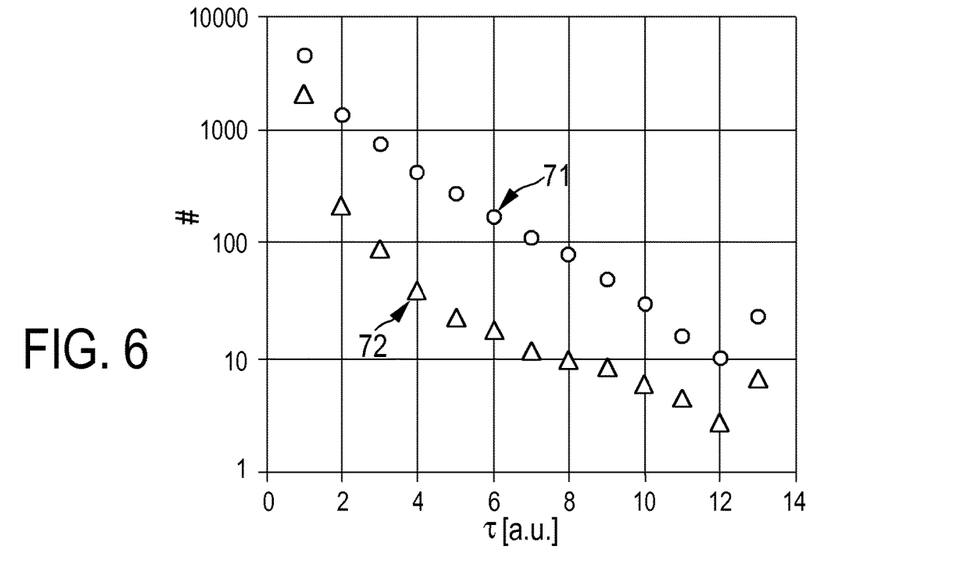
FIG. 6 shows schematically and exemplarily a histogram of lifetimes of location events.
Figure 7:
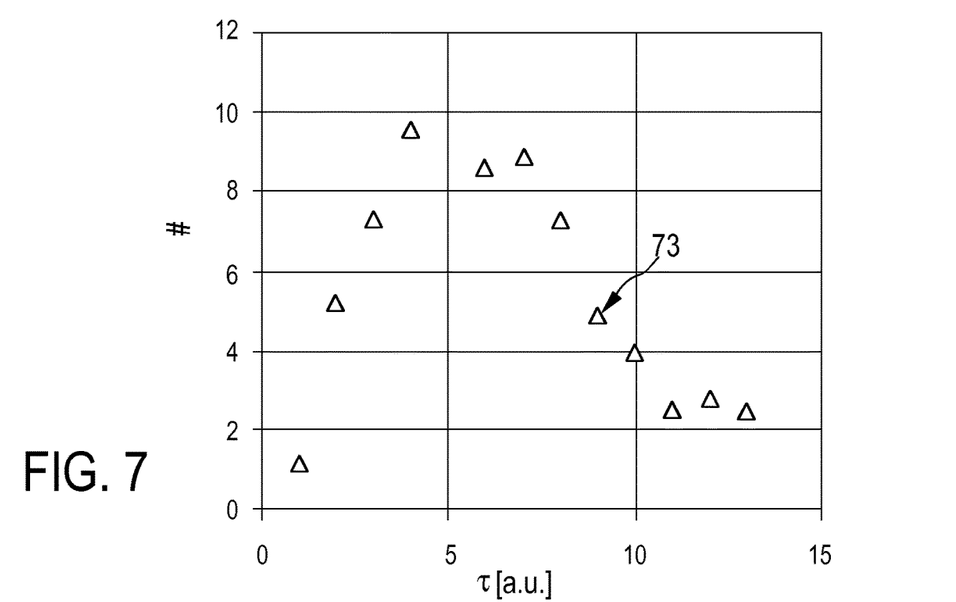
FIG. 7 shows schematically and exemplarily a ratio of two histograms of lifetimes of location events.

For example, the substance can be a protein in blood plasma being the fluid. A first measurement can be performed with the protein in the blood plasma, wherein the concentration of the protein in the blood plasma can be, for example, 5 pM, and a second measurement can be performed without the protein. Two resulting lifetime histograms are exemplary shown in FIG. 6. In FIG. 6, the number # of location events is shown depending on their lifetimes $\tau$ in arbitrary units. The first lifetime histogram is denoted by 71 and the second lifetime histogram is denoted by 72. FIG. 7 shows the corresponding ratio 73 of the first lifetime histogram 71 to the second lifetime histogram 72. The maximum of the ratio 73 is at $\tau=5$, wherein, in an example, this maximum can correspond to $\tau=20$ s. The lifetime range can be predefined such that this maximum is within the predefined lifetime range. For instance, the predefined range can have a predefined absolute or relative temporal length, wherein this range having a predefined absolute or relative length, is centered on the maximum lifetime.

By determining the predefined lifetime range such that the maximum of the figure of merit, in particular, the ratio of specific location events and non-specific location events, which corresponds to a ratio of a first measurement with the substance to be determined and a second measurement without this substance, is within the lifetime range, the limit of detection of the substance determining apparatus can be increased, wherein the limit of detection can be defined as the lowest concentration of a substance like a protein, which reliably can be measured above a background level.

In general not only particles bound to the binding surface 30 will be detected but also particles which are very close to the binding surface 30. Basically particles are visible when they are present in the sensing region on the binding surface 30, which is, in this embodiment, defined by the evanescent field of an incoming light beam. These particles do not have a molecular bond to the surface but move in close proximity of the binding surface. Due to the movement of these free particles in and out of the sensing region, they correspond to particles with a very short lifetime. In essence it is not the lifetime of a real molecular bond but it is a lifetime in the sensing region. Since the particles move, they show up at continuously different positions. By filtering these short lifetimes from the signal, the contribution of these free particles to the signal can be removed or at least decreased.

Also bound particles have the possibility to move over a short distance because of the finite bond length. This can cause continuous changes in the sensing signal. Small particles which have an intensity slightly above the background signal can appear and disappear due to the intensity fluctuations, showing a similar behaviour as the free particles. There is however one large difference: the bound particles will appear and disappear at approximately the same position, i.e. within a same region having a predefined size, while the free particles will appear and disappear at different positions, i.e. not within a same region having the predefined size. The size of the same region can be determined by, for example, calibration measurements such that bound particles appear and disappear within a same region and the free particles appear and disappear within and outside a same region having the predefined size.

The substance determination unit 70 is therefore preferentially further adapted to determine the substance within the fluid based on location events, which succeed each other in the same region on the binding surface with a temporal duration being smaller than a predefined temporal duration threshold and which have lifetimes being smaller than a lifetime threshold, in order to discriminate bound fluctuating particles from free fluctuating particles. Thus, the substance determination unit 70 can be adapted to determine the substance within the fluid based on these lifetimes and the lifetimes within the predefined lifetime range.

The location event determination 134 is preferentially adapted to perform an image analysis for determining the location events. In particular, the detectors 21 and 27 provide images showing a gray scale pattern. A recognition algorithm for recognizing bright spots in the grey scale pattern is applied for recognizing particles within the sensing region on the binding surface 30. The bright spots may be caused by bound particles or by unbound particles located within the sensing region. Moreover, scratches or dirt on the binding surface 30 may appear as an elevated intensity in the respective image. Depending on the thickness, intensity and direction of the scratch or dirt on the binding surface, they may be recognized as particles within the sensing region, leading to location events having a lifetime distribution with predominantly large lifetimes. The predefined lifetime range is preferentially predefined such that relatively large lifetimes of location events, which are related to artifacts on the binding surface like scratches and/or dust, are substantially not within the predefined lifetime range.

The substance determination unit 40 is preferentially adapted to determine the substance within the fluid based on the number of location events with lifetimes within the predefined lifetime range. In particular, assignments between concentrations of the substance within the fluid and the number of location events having lifetimes within the predefined lifetime range, can be determined by calibration measurements, wherein the number of these location events is determined, while the concentration of the substance within the fluid is known. The substance determination unit 14 can then be adapted to determine the concentration of the substance within the fluid based on the number of location events having lifetimes within the predefined lifetime range and the assignments.

Referring again to FIG. 4, the substance determination apparatus 19 is comprised of the binding device 1 and the analyzing device 18. The binding device 1 is, in this embodiment, a cartridge including the particles and the binding surface 30 and being adapted to receive the fluid 3. The analyzing device 18 can be regarded as a reader and includes the sensing unit 33, the location event determination unit 34, the location events selection unit 70 and the substance determination unit 40. The binding device 1 is a disposable device and the analyzing device 18 is a re-useable device.

The analyzing device 18 further comprises an output unit 60 for outputting a value indicating the amount or concentration of the substance within the fluid. The output unit 60 is preferentially a display. The analyzing device 18 further comprises a control unit 61 for controlling the sensing unit 33, the location event determination unit 34, the location events selection unit 70, the substance determination unit 40 and the output unit 60.

As already mentioned above, the binding device 1 is preferentially a cartridge for receiving a fluid like blood, saliva or urine, for filtering the fluid and for transferring the filtered fluid to the sensing site of the cartridge. The cartridge is disposable and is adapted for single use only. The analyzing device 18 is adapted to be used several times with different cartridges. Thus, a fluid 3 like blood, saliva or urine is put on the filter element 2 of the binding device 1, the fluid 3 is filtered and the filtered fluid is transferred to the sensing location 7. The binding device 1, i.e. in this embodiment the cartridge, is arranged in the analyzing device 18 and a substance within the fluid 3 at the sensing location is analyzed by the analyzing device 18. After the binding device 1 has been used, it is preferentially discarded, whereas the analyzing device 18 is used for a next analyzing procedure.

Figure 8:
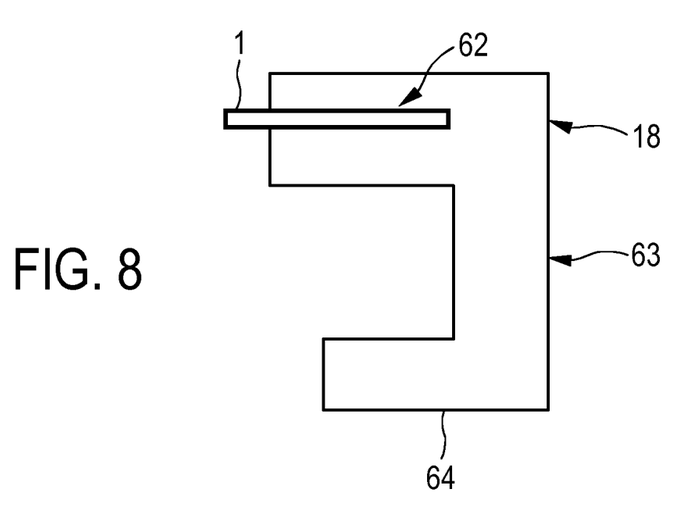
FIG. 8 shows schematically and exemplarily a binding device introduced into an analyzing device.

The several units of the analyzing device 18 are preferentially arranged within a casing 64, which is schematically and exemplarily shown in FIG. 8 and which can comprise a grip part 63 for allowing a user to hold the analyzing device 18 in the hand while analyzing the substance in the fluid. The casing 64 comprises a receiving section 62 for receiving the binding device 1. In other embodiments, the casing 64 can have another shape.

The several units of the analyzing device 18 can also be arranged within a casing not being a handheld casing. For example, the casing of the analyzing device can be adapted to stand on a table or the like.

Figure 9:
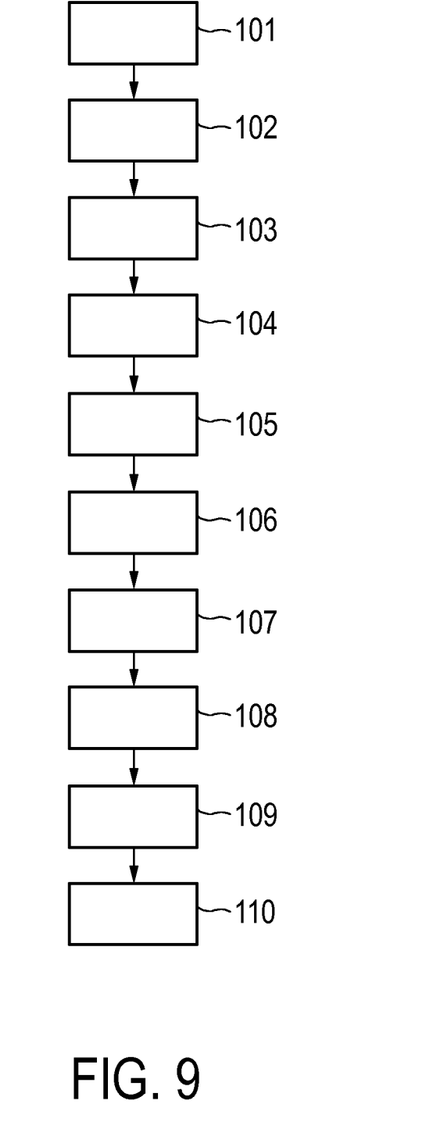
FIG. 9 shows a flowchart exemplarily illustrating an embodiment of a substance determining method for determining a substance in a fluid.

In the following, an embodiment of a substance determining method for determining a substance within a fluid will exemplarily be described with reference to a flowchart shown in FIG. 9.

In step 101, a fluid comprising a substance is arranged on the filter element 2. In step 102, the fluid is filtered by the filter element 2, and, in step 103, the filtered fluid is transferred to the sensing location 7 by capillary forces generated by the connecting channel and the guiding channels of the capillary structure. Before, while or after performing steps 101 to 103, the binding device 1 has been introduced into the analyzing device 18. At the sensing location 7, magnetic particles coated with a specific antibody, that attaches to a target molecule, i.e. the substance, present in the fluid, are located. They mix with the filtered fluid and attach to the target molecules within the fluid in step 104. In step 105, the particles bind to the binding surface 30, if the particles have been attached to the substance, and, in step 106, the particles within a sensing region on the binding surface are sensed by the sensing unit, wherein a sensing signal is generated depending on the particles in the sensing region. In step 107, location events, which indicate that a particle is located in the sensing region, and their lifetimes in the sensing region are determined from the generated sensing signal by the location event determination unit. In step 108, a part of the location events is selected having lifetimes in a predefined lifetime range by the location event selection unit, and, in step 109, the substance within the fluid is determined based on the selected part of the location events by the substance determination unit. In step 110, the determined substance, in particular, the determined amount and/or concentration of the substance, within the fluid is shown on the output unit 60.

Steps 101 to 105 can be regarded as the steps of a binding method, and steps 106 to 110 can be regarded as the steps of an analyzing method.

The substance determining apparatus can be adapted such that the filtering of the lifetime distribution at least partially removes information, which is not specific to the binding of particles, which have been attached to the substance to be detected, like information caused by non-specific bonds, free particles, weakly-bound particles and ghost particles caused by scratches or other surface artifacts. This removal of non-specific information can lead to a substantially proportional relation between the concentration of the substance, i.e. the target molecules, in the fluid and the number of filtered location events. In particular, the number of filtered location events can be less sensitive to variations in a non-specific binding.

The substance determining apparatus method can be adapted to determine the lifetime distribution, for example, during the binding phase or during the washing phase. Since the number of location events is larger during the binding phase, using the substance determining apparatus and method during the binding phase can offer statistical advantages with respect to the use of the substance determining apparatus and method during the washing phase.

Although, in an above described embodiment, the lifetime histogram is filtered such that the influence of scratches and/or dirt on the determination of the substance within the fluid is reduced or even eliminated, the filtering can also be performed such that the influence of other surface artifacts on the determination of the substance within the fluid is reduced or even eliminated like the influence of, for example, bubbles on or within the binding surface.

The filtering is performed by using a predefined lifetime range, wherein location events having lifetimes within the predefined lifetime range are selected for determining the substance within the fluid. This predefined lifetime range can be arranged such that only location events having lifetimes being larger than a threshold, only location events having lifetimes being smaller than a threshold or both, location events having lifetimes being smaller than a smaller threshold and location events having lifetimes being larger than a larger threshold, are filtered out.

The substance determining apparatus and method can be adapted to use only a single predefined lifetime range or several predefined lifetime ranges.

The substance determining apparatus and method can be adapted for the detection of DNA, in particular, in molecular diagnostics, proteins, or other substances within a fluid.

The binding device can be an optical cartridge being a carrier of a bioassay comprising particles being optical labels, preferably microscopic super-paramagnetic labels providing optical contrast by means of scattering and/or fluorescence.

Although in the above described embodiments total internal reflection has been used for inducing the evanescent field, in other embodiments other techniques can be used for inducing the evanescent field, for example, grating coupling or waveguide coupling can be used.

Although in the above mentioned embodiment described with reference to FIG. 4, a microscope objective 32 has been used, in other embodiments another objective lens for collecting and imaging of photons can be used. This objective lens is positioned at the bottom side of the binding device, underneath the horseshoe actuation magnet 23. The photons from the optical labels are transmitted through an air gap in between the two horseshoe magnets 23, before they are captured by the objective lens. The objective lens has a numerical aperture allowing imaging the individual optical labels onto the second light detector 27 being, for example, a CCD camera.

Although in the above described embodiments the substance determining apparatus comprises means for generating FTIR sensing signals and DFM sensing signals, in other embodiments the substance determining apparatus can be adapted such that it comprises only one of these means, i.e. means for generating FTIR sensing signals or means for generating DFM sensing signals, as long as the generated sensing signals allow the location event determination unit to determine location events indicating occurrences of particles within the sensing region on the binding surface, in particular, lifetimes of the location events, from the generated sensing signal.

Although in the above described embodiments the lifetime has been determined as a property of the location events, wherein a part of the location events is selected having a lifetime in a predefined lifetime range, in other embodiments another property of the location events can be determined, wherein location events can be selected having a property within a corresponding predefined property range. For example, at least one of a starting moment, an ending moment, a positional variation of the respective particle in the sensing region, and a size of a respective location event in the respective image can be determined as a property of a location event. In particular, the location event determination unit can be adapted to determine several properties for a location event, wherein the location event selection unit can be adapted to select a part of the location events having properties within the respective property ranges. For example, the location event selection unit can be adapted to select only location events having all properties within the respective property ranges.

The respective property range is preferentially determined by measuring the properties for specific and non-specific binding, wherein the property range is predefined such that the influence of the non-specific binding on the signal is minimized.

The property range for the starting moment is preferentially chosen such that binding conditions are substantially constant, wherein such a property range is also preferentially determined by experimental measurements. For example, if a wet assay is performed, in which a fluid with magnetic particles is injected in a fluidic channel of a cartridge, wherein during the assay a magnetic actuation is performed, magnetic particles are collected near the sensing region when the magnetic actuation is started. Thus, in the beginning the magnetic particle concentration may not be constant above the sensing region. The property range regarding the starting moments is preferentially chosen such that only starting moments are selected, which correspond to times being larger or equal to the moment from which on the magnetic particle concentration is substantially constant. Location events can therefore be excluded, which correspond to particles which have been bound under undefined or unstable conditions.

Each particle whether bound or not bound will exhibit Brownian motion, i.e. a random movement. A bound particle will also show random movement, but because the particle is bound, the movement is around the position of the bound. The amount of movement or positional variation is influenced by, for example, the length of the bond, for example, a longer bond will allow more freedom of movement, and/or the number of bonds. For instance, a particle may be bound with a single bond, but also with multiple bonds. Multiple bonds will restrict the movement of the particle more than a single bond. In an embodiment, the property range regarding the positional variation can be predefined such that location events are selected having a positional variation, which corresponds to a certain kind of binding.

Although in a described embodiment the analyzing device is a handheld device, in other embodiments the analyzing device can also be a standalone system which is to be arranged on, for example, a table.

In the above described embodiment, the fluid was preferentially blood. In other embodiments, the fluid can be any other fluid, in particular, another body fluid, like saliva or urine. The preferred application for the binding device and for the analyzing device is in the field of point-of-care diagnostics, in particular, based on a finger prick blood sample, like a cardiac marker detection application. But, as mentioned above, the binding device can also be adapted for being used with other fluids like saliva for Drugs Of Abuse.

In the above described embodiments, the analyzing device apparatus uses evanescent field techniques for determining the amount of magnetic beads, i.e. magnetic particles, in the sensing region on the surface. In other embodiments, other techniques can be used for determining these beads. For example, magnetic methods, sonic detection, electrical detection and combinations therefore can be used. Furthermore, the analyzing device can comprise any sensor which based on the detection of the magnetic properties of the beads on or near to the binding surface. The analyzing device can be adapted for detecting molecular targets, which often determine the concentration and/or presence of larger moieties, for example, cells, viruses, fractions of cells or fractions of viruses, tissue extract et cetera. The magnetic beads can be detected directly by the sensing method. As well, the particles can be further processed prior to detection. An example of further processing is that materials are added or that the chemical, biochemical or physical properties of the magnetic labels are modified to facilitate detection. The analyzing device can be adapted for working together with several biochemical assay types, for example, binding/unbinding assay, sandwich assay, competition assay, displacement assay, enzymatic assay et cetera. The binding device and the analyzing device can be adapted for sensor multiplexing, i.e. the parallel use of different sensors and sensor surfaces, label multiplexing, i.e. the parallel use of different types of labels, and chamber multiplexing, i.e. the parallel use of different reaction chambers. The binding device and the analyzing device can be used as rapid, robust and easy to use point-of-care biosensors for small sample volumes. The sensing cavity is preferentially a part of a disposable cartridge, which is to be used with the analyzing device, which contains one or more magnetic field generating means, i.e. the magnetic unit, and one or more detection means. The binding device and the analyzing device can preferentially be adapted for use in automated high-throughput testing.

The particles are preferentially magnetic beads being preferentially nanoparticles having at least one dimension ranging between 3 nm and 5000 nm, preferably between 10 nm and 3000 nm, more preferred between 50 nm and 1000 nm.

Although in the above described embodiments a certain binding device and a certain analyzing device have been described, in other embodiments the binding device and the analyzing device can have another structure. For example, the binding device can just comprise a binding surface. Or another kind of filter for filtering the fluid can be used or another channel structure can be used for transferring filtered fluid from a filter location to a sensing location.

Although in the above described embodiments the substance determining apparatus is comprised of a binding device and an analyzing device, in another embodiment the substance determining apparatus can be an integrated apparatus comprising at least the particles, the binding surface, the sensing unit, the location event determination unit, the location events selection unit and the substance determination unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of location events and their lifetimes or the determination of the substance, in particular, of the amount and/or concentration of the substance, within the fluid performed by one or several units or devices can be performed by any other number of units or devices. For example, steps 107 to 109 can be performed by a single unit or by any other number of different units. The determinations and/or the control of the substance determining apparatus, in particular, of the analyzing device, in accordance with the substance determining method, in particular, in accordance with the analyzing method, can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a substance determining apparatus for determining a substance within a fluid. A location event determination unit determines location events indicating that a particle, which may have attached the substance, is located in a sensing region and a property of the location events from the sensing signal generated by sensing the sensing region. A location events selection unit selects a part of the location events having a property in a predefined property range, and a substance determination unit determines the substance within the fluid based on the selected part of the location events. This allows tuning the determination of the substance within the fluid to a desired property range, which can relate to a desired kind of bound particles, thereby reducing the influence of unwanted effects on the determination of the substance and, thus, improving the determination accuracy.

The invention claimed is:

1. A substance determining apparatus for determining a substance within a fluid, the substance determining apparatus comprising:
    particles configured to bind to the substance within the fluid,
    a binding surface to which the particles are configured to bind if the particles have been attached to the substance,
    a sensor configured to sense the particles within a sensing region on the binding surface, wherein the sensor is adapted to generate a sensing signal depending on the particles in the sensing region, and
    computing hardware programmed to perform a substance determining method including:
        determining location events indicating that a particle is located in the sensing region on the binding surface and lifetimes of the location events from the sensing signal generated by the sensor,
        selecting a part of the location events having a lifetime in a predefined lifetime range, and
        determining the substance within the fluid based on the selected part of the location events.

2. The substance determining apparatus as defined in claim 1, wherein the substance determining method further determines at least one of the following properties of the respective location event: starting moment, ending moment, size, and positional variation of the respective particle in the sensing region.

3. The substance determining apparatus as defined in claim 1, wherein the substance determining method further determines several properties of a respective location event and the selecting comprises selecting a part of the location events having all said several properties within respective property ranges.

4. The substance determining apparatus as defined in claim 2, wherein the generated sensing signal is indicative of starting moments and ending moments of location events and wherein the determining of location events includes determining the lifetimes of location events by determining the starting moments and the ending moments of the location events from the generated sensing signal.

5. The substance determining apparatus as defined in claim 2, wherein the sensor comprises an imaging unit configured to generate images of the binding surface at different times as the sensing signal, wherein an image shows at which positions on the binding surface particles are located at a time, wherein the at least one of the following properties of the respective location event:
- the starting moment by comparing temporally consecutive images,
- the ending moment by comparing temporally consecutive images,
- the size of a respective location event in the respective images, and
- the positional variation of the respective particle in the sensing region by tracking the respective particle in temporally consecutive images.

6. The substance determining apparatus as defined in claim 5, wherein the sensor comprises:
- a light source arranged to generate radiation directed to the binding surface for generating an evanescent field, which defines the sensing region; and
- a light detector arranged to detect light from the binding surface, wherein the detected light has been influenced by the particles located on the binding surface by influencing the evanescent field and wherein the images are generated from the detected influenced light.

7. The substance determining apparatus as defined in claim 1, wherein the sensor comprises a force applying unit for applying a force to the particles for putting bindings between the particles and the binding surface under stress, while sensing the particles.

8. The substance determining apparatus as defined in claim 7, wherein the determining of location events includes:
- determining a particles signal being indicative of the number of particles in the sensing region from the sensing signal,
- differentiating the particles signal, and
- determining a distribution of location events depending on their lifetime in the sensing region from the differentiated particles signal,
wherein the selecting includes selecting the part of the location events having a lifetime within a predefined lifetime range being the predefined property range based on the determined distribution of location events.

9. The substance determining apparatus as defined in claim 1, wherein the predefined lifetime range is predefined such that a figure of merit, which is indicative of a ratio of a specific histogram of lifetimes of specific location events being binding events, which relate to bindings of particles having been attached to the substance, and a non-specific histogram of lifetimes of non-specific location events, which relate to other location events, has an optimum within the predefined lifetime range.

10. The substance determining apparatus as defined in claim 1, wherein the predefined lifetime range is predefined such that a probability that the lifetime of location events, which are related to at least one of unbound particles, other elements and artifacts on the binding surface, is not within the predefined lifetime range is larger than a probability that lifetimes of location events, which are related to at least one of unbound particles, other elements and artifacts on the binding surface, is within the predefined lifetime range.

11. The substance determining apparatus as defined in claim 1, wherein the computing hardware comprises a computer configured to perform the substance determining method.

* * * * *